United States Patent [19]

Schütze

[11] Patent Number: 5,689,109
[45] Date of Patent: Nov. 18, 1997

[54] APPARATUS AND METHOD FOR THE MANIPULATION, PROCESSING AND OBSERVATION OF SMALL PARTICLES, IN PARTICULAR BIOLOGICAL PARTICLES

[76] Inventor: Raimund Schütze, Sudetenstrasse 22, Wolfratshausen, Germany, 82515

[21] Appl. No.: 295,740

[22] PCT Filed: Jan. 13, 1994

[86] PCT No.: PCT/EP94/00090

§ 371 Date: Aug. 30, 1994

§ 102(e) Date: Aug. 30, 1994

[87] PCT Pub. No.: WO94/16543

PCT Pub. Date: Jul. 21, 1994

[30]     Foreign Application Priority Data

Jan. 13, 1993 [DE] Germany ............................ 43 00 698.1

[51] Int. Cl.[6] ......................................................... H05H 3/04
[52] U.S. Cl. ............................................. 250/251; 359/350
[58] Field of Search ................................ 250/251; 359/350

[56]     References Cited

U.S. PATENT DOCUMENTS 4,893,886  1/1990  Ashkin et al. .......................... 350/1.1

FOREIGN PATENT DOCUMENTS

| 437 043 A2 | 7/1991 | European Pat. Off. ........ G02B 21/32 |
| 517 454 A3 | 12/1992 | European Pat. Off. ......... H05H 3/04 |
| 552 539 A2 | 7/1993 | European Pat. Off. ......... H01S 3/05 |
| 317 167 | 7/1991 | Japan ................................. C12M 1/00 |

OTHER PUBLICATIONS

Steubing et al., SPIE, vol. 1202, 272–280 (1990).
Ashkin et al., NATURE, vol. 330, 769–771 (1987).
Ashkin et al., Ber. Bunsenges. Phys. Chem., 254–260 (1989).

Primary Examiner—David P. Porta
Assistant Examiner—Richard Hanig
Attorney, Agent, or Firm—Ernest V. Linek

[57]     ABSTRACT

Apparatus for the manipulation, processing and observation of small particles, in particular biological particles, is disclosed. A first laser (4) generates light beams in a first wavelength range, which are focused with a first optical device (12, 13; 14, 15) and form an optical trap. A object holder (22) serves to contain the relevant particles. In addition a light source (17) for observation light is provided, whereas observation and recording devices serve to observe particles and record their behavior. A second laser (3) generates light beams in a second wavelength range, which are focused in order to manipulate particles in the object holder. The optical devices for the individual light beams can be positioned and focused independently of one another, and at the beginning of manipulation and observation the beams are focused in the same object plane of the object holder independently of their wavelengths.

24 Claims, 1 Drawing Sheet

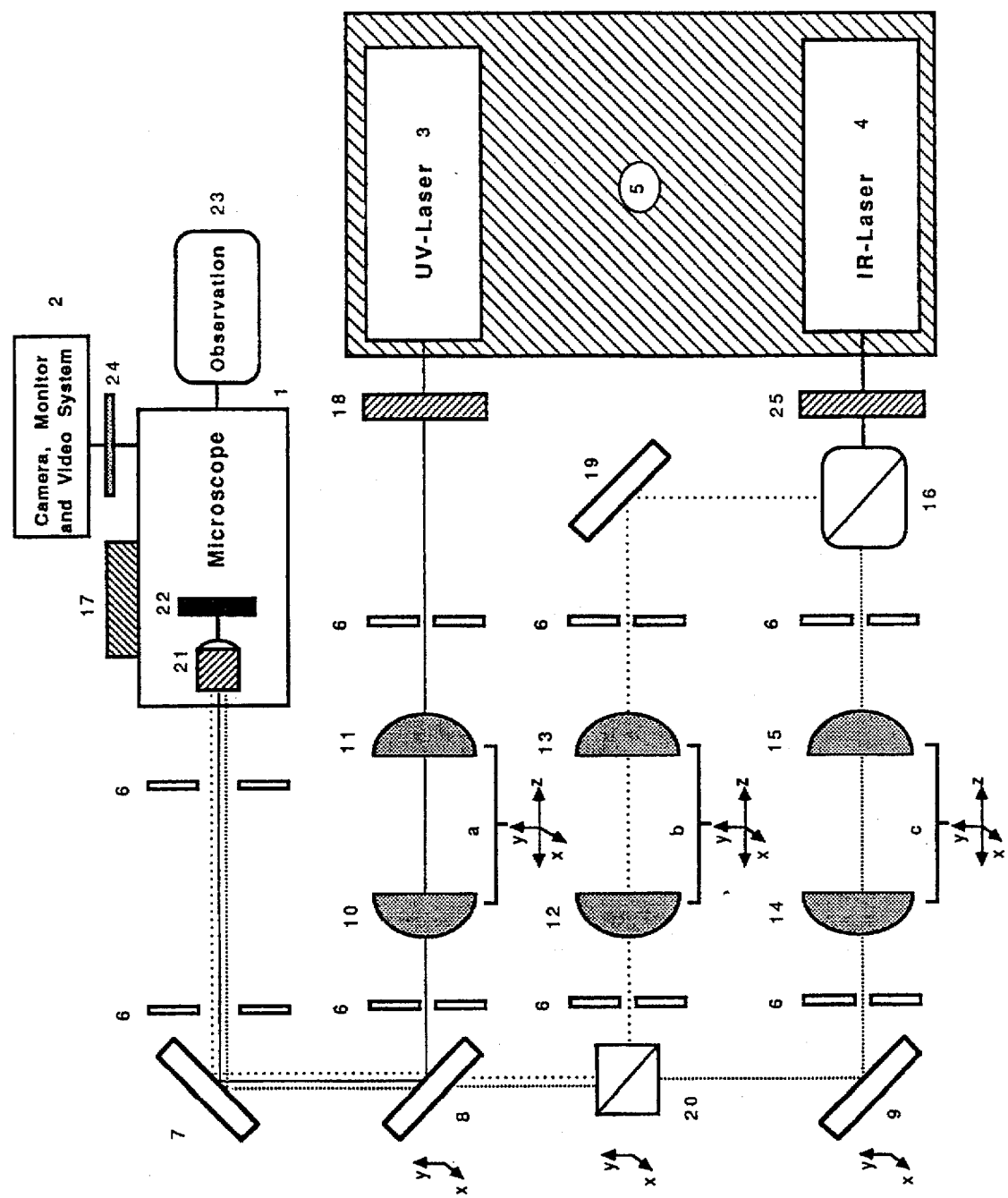

APPARATUS AND METHOD FOR THE MANIPULATION, PROCESSING AND OBSERVATION OF SMALL PARTICLES, IN PARTICULAR BIOLOGICAL PARTICLES

The invention relates to apparatus for the manipulation, processing and observation of small particles, in particular biological particles, comprising at least one first laser, which generates light beams in a first wavelength region that are focused by a first optical device with sufficient convergence to form an optical trap in a given region; an object holder to contain particles, in particular biological particles; a light source for observation light; and observation and recording devices with which to observe the particles in the object holder and record their behavior.

The invention further relates to a method for the manipulation, processing and observation of small particles, in particular biological particles, in which the objects in an object holder are fixed in an optical trap by at least one first laser, which generates light beams in a first wavelength range, and the objects are observed and/or their behavior recorded with observation and recording devices.

Apparatus of this kind is known, for example, from U.S. Pat. No. 4,893,886, which employs a so-called optical trap that uses a strongly focused laser beam with an intensity profile having an approximately Gaussian distribution. In these optical traps the components of radiation pressure, namely scattering force and gradient force, are combined with one another to form a point of stable equilibrium situated close to the focus of the laser beam. Here the scattering force is proportional to the optical intensity and acts in the direction of the incident laser light. The gradient force is proportional to the optical intensity and points in the direction of the intensity gradient.

Details of such optical traps and their physical bases are given, for example, in the publication "Optical Trapping and Manipulation of Single Living Cells Using Infra-Red Laser Beams", A. Ashkin et al. in BERICHTE DER BUNSEN-GESELLSCHAFT FOR PHYSIKALISCHE CHEMIE, March 1989, pp. 254–260.

Apparatus of this kind can be used to capture, fix and manipulate small particles, in particular biological particles, which can otherwise move freely in a fluid within the object holder. One difficulty that arises here is that of simultaneously observing the particles as they are being manipulated in order to enable precise processing.

The invention is therefore directed to the problem of providing an apparatus and a method by which well-directed and exact manipulation, processing and observation of small particles, in particular biological particles, can be achieved.

Thus, in accordance with the present invention there is provided an apparatus of the kind mentioned at the outset characterised in that of at least one second laser is provided, which generates light beams in a second wavelength range that are focused by a second optical device with sufficient convergence to manipulate particles present in the region of the object holder; in that the optical devices for the light beams in the first wavelength range, for the light beams in the second wavelength range and for the beams of the observation light are each separate and can be positioned and focused independently of one another; and in that the light beams in the first wavelength range, the light beams in the second wavelength range and the beams of the observation light are focused in the same object plane of the object holder at the beginning of the manipulation and observation, regardless of their wavelengths.

As a further development of the apparatus in accordance with the invention, it is provided that each of the first lasers is of an adjustable-wavelength type as appropriate, in particular an IR laser, and that each of the second lasers is an adjustable-wavelength UV laser as appropriate, in particular a pulsed UV laser. By this means the particles can be fixed suitably for practical purposes while the actual manipulation is performed with the UV laser, with no danger that excessive amounts of energy will be applied, which could otherwise cause undesirable damage to the particles.

According to a special embodiment of the apparatus in accordance with the invention, it is provided that each of the first lasers is a Nd:YAG laser, a Nd:YLF laser or a titanium-sapphire laser and each of the second lasers is a nitrogen laser, a frequency-multiplied IR laser or a pumped dye laser.

As a further development of the apparatus in accordance with the invention, it is provided that all of the first lasers and the second lasers are disposed in the same tower but can be positioned and adjusted independently of one another. The basic arrangement of the light sources can thus be achieved in a space-saving manner, especially when the lasers of the two types are disposed one above the other on appropriate mounting plates. The components of the focusing and deflecting optics in turn can be mounted together on a single plate associated with the tower, to achieve a compact structure.

The light sources that generate light beams in the particular wavelength ranges can be provided as separate lasers. In a preferred embodiment of the apparatus in accordance with the invention it is provided that the beam of the first laser is split with a beam splitter to produce at least first and second light beams in the first wavelength range, which are sent along separate paths, at least in part, and then directed onto the object in the object holder. If needed, additional light beams can be diverted from the beam of the first laser with such a beam splitter, separately guided, at least in part, and then directed onto the object in the object holder, when several such beams are to be used as an optical trap.

In a special embodiment of the apparatus in accordance with the invention it is provided that the beam splitter is a polarizing beam splitter, which produces a first beam with s-polarized light and a second beam with p-polarized light and adjusts the phase shift between these two light beams, and that the percentage relationship between the intensities of the two light beams in the first wavelength range is adjustable.

In the apparatus in accordance with the invention it proves useful to provide each of the beams from the first laser and the second laser with its own diverging optic, each of which can be adjusted in three dimensions, in particular on three orthogonal coordinates.

It is also useful in the apparatus in accordance with the invention for the mirrors and beam splitter in the paths of the beams of the first laser and the second laser to be rotatable or tiltable independently of the diverging optics. This feature offers the advantage of an additional means of adjusting the individual beams in the x-y plane.

In a further development of the apparatus in accordance with the invention, the beam of the observation light can be focused on the object in the object holder by adjusting the objective and/or the object holder along the optical axis, in the z direction, and the observed site, illuminated by the beam of the observation light in the object plane, can be adjusted by displacing the object holder in an x-y plane within the object plane.

It is further advantageous to provide a beam attenuator in the path of each beam from the first lasers and second lasers, by means of which the beams in the respective wavelength ranges can be attenuated, either in preset steps or continuously, before they are directed onto the object in the object holder. The intensity of these beams can thus be adjusted to a level such that undesirable damage of particles is avoided.

It is especially advantageous in the apparatus in accordance with the invention for the beams in the first. wavelength range and the beams in the second wavelength range to be directed onto the object in the object holder through a common objective by way of a common mirror. This arrangement enables a particularly compact structure of the apparatus. At the same time the configuration of the beam path is simplified and reliable operation of the apparatus is ensured.

In a special embodiment of the apparatus in accordance with the invention it is provided that the light beams produced by the beam-generating devices and subsequently treated, deflected and focused on the object all lie substantially the same first plane, that the object holder is situated in a second plane, perpendicular to the first plane, and that the mirrors or beam splitters to divert the individual beams are also disposed in planes perpendicular to the first plane. This makes available an especially compact and easily handled apparatus, which guarantees reliable coordination of the individual light beams.

The method in accordance with the invention is characterized in that at least one second laser is employed, which generates beams in a second wavelength range that are focused with sufficient convergence to manipulate particles present in the region of the object holder; in that the beams in the first wavelength range, the beams in the second wavelength range and the beams of an observation light can each, independently of one another and with separate optical devices, be adjusted in the object plane, the so-called x-y plane, and focused in the axial, so-called z direction, perpendicular to the x-y plane; and in that at the beginning all the above-mentioned light beams are focused in the same object plane of the object holder independently of their wavelengths.

The method in accordance with the invention provides an advantageous way of permitting the user of a corresponding apparatus to employ a stable starting position and orient himself to the plane in which events are occurring or are to be influenced.

In a further development of the method in accordance with the invention it is provided that a particle caught in the optical trap of the first laser can be moved (a) by displacing at least one light beam in the first wavelength range in the x-y direction and/or (b) by displacing the object holder in the x-y direction in the object plane, only the trapped particle being moved in case (a) and all the particles in case (b).

It is also provided in a further development of the method in accordance with the invention that a particle caught in the optical trap of any of the first lasers can be moved (a) by displacing at least one light beam in the first wavelength range in the z direction and/or (b) by displacing the objective and/or the object holder in the z direction, so that in case (a) the trapped particle is moved out of the chosen observation plane and in case (b) the trapped particle remains in the chosen observation plane.

Of course, not only linear displacements of particles are possible; rather, in a further development of the method in accordance with the invention, with the use of at least two separate beams in the first wavelength range a particle in the optical trap can be rotated, by (a) leaving one beam in its starting position and moving the other in the x-y direction, or (b) leaving one beam in its starting position and moving the other in the z direction, or (c) moving at least two beams in opposite directions or over different distances along the z axis, or (d) combinations of the movements in (a), (b) and (c).

In a further development of the method in accordance with the invention it is provided that the particles are manipulated with the beams in the second wavelength range in an arbitrarily selectable x-y plane of the object holder, which may be the same as the observation plane or another plane parallel to it. This sort of alteration off the observation plane is readily achievable, after the starting position has been established at the beginning of the procedure.

In the method in accordance with the invention it is advantageous to use visible or IR laser beams for fixing the particles in the optical trap and UV laser beams, in particular pulsed UV laser beams, for manipulating the particles.

When in a further development of the method in accordance with the invention all the light beams are directed simultaneously through the same objective onto the object in the object holder, especially reliable adjustment and manipulation become possible.

Finally, in the method in accordance with the invention all the light beams for controlling the treatment and/or observation can be adjusted in their intensity and/or turned on and off independently of one another. This is an advantageous means of providing many possibilities for the manipulation, processing and observation of particles.

In the following, the invention is explained in detail, also with respect to additional characteristics and advantages, by the description of an exemplary embodiment and with reference to the attached drawing.

BRIEF DESCRIPTION OF THE DRAWINGS

The single figure in the drawing is a schematic representation of an embodiment of apparatus in accordance with the invention, showing the light sources used and the beam paths.

DETAILED DESCRIPTION OF THE INVENTION

In the drawing there can be seen a common laser tower 5 in which are disposed, advantageously one above the other, an IR laser 4 as first laser and a UV laser 3 as second laser. On a common mounting plate there can be disposed several rails with associated lifting devices for the corresponding optical components, so that the latter can be adjusted relative to the two lasers 3 and 4 in such a way that the light beam each laser emits in its own wavelength range passes through the subsequent optical devices to the object holder 22. Here it is advantageous for the lasers 3 and 4 to generate parallel beams. The optical components on their rails can usefully be of modular design.

In the illustrated embodiment the IR laser 4 generates a light beam that is divided by the beam splitter 16 into a first beam and a second beam. The first beam goes through corresponding diaphragms 6 and a diverging optic 14, 15 and is then deflected by an IR-reflecting mirror 9, after which it passes through a beam splitter, e.g. a prism or a half-silvered mirror 20, and another half-silvered mirror 8 or a corresponding prism. It is then directed by a deflecting mirror 7 to a schematically indicated microscope 1 with an objective 21, a object holder 22 and a light source 17 for observation light.

The split-off part of the beam from the IR laser 4 passes from the beam splitter 16 to a mirror 19 which directs it through corresponding diaphragms and a second diverging optic 12, 13. Then this second beam is deflected by the beam splitter or half-silvered mirror 20 and led to the microscope 1 in the same way as the first beam from the IR laser 4.

To produce the second light beam in the first wavelength range it is also possible, of course, to use an additional IR laser, not shown. Although this arrangement offers additional possibilities with respect to intensity, polarization, wavelength and controllability of such a laser beam, it makes the apparatus more elaborate and expensive, so that in practice a problem-oriented decision must be taken.

In the illustrated embodiment the beam splitter 16 can be a simple beam splitter, in which case with sufficient output from the IR laser and intensity of the light beam some of the intensity is drawn off for the second beam. In a preferred embodiment, however, the beam splitter 16 has the form of a polarizing beam splitter, which generates a first beam with s-polarized light and a second beam with p-polarized light and adjusts the phase shift between these two beams, the percentage relationship between the intensities of the two beams in the first wavelength range of the IR laser 4 being simultaneously adjustable.

It is advantageous for the optical components used in this region to be coated for infrared light, to guarantee that the beams are directed precisely without undesired losses. If desired, a beam attenuator 25 can be provided in the path of the first and/or second beam, so that the power of the light beam can be adjusted. Alternatively or additionally, it is possible to adjust the output of the IR laser 4 itself within a preset range.

Independently thereof, in the path of the first and second beams from the IR laser 4 means are provided for interrupting the respective beam. Either the diaphragms 6 or separate closing devices can be used for this purpose.

As second laser a UV laser 3 is provided, which generates a beam in a second wavelength range that passes through a beam attenuator 18, diaphragms 6 and its own diverging optic 10, 11, and then is deflected by the mirror 8 and the subsequent mirror 7 so as to reach the objective 21 and the object holder 22. The UV laser 3 is advantageously a pulsed UV laser, so that the energy supplied by the UV light can be precisely adjusted and controlled, to prevent damage to the objects being manipulated.

The beam attenuator 18 additionally serves to attenuate the light beam in the second wavelength range (UV light) either in preset steps or continuously. The beam attenuator 18 can thus be an adjustable filter or a beam splitter.

The components situated in the beam path of the UV laser 3 are of course designed and suitable for such UV light, and the components 7 and 8 as well as 21 are designed for both IR and UV light and are correspondingly coated.

Associated with the microscope 1 are a light source 17 for observation light, which is advantageously visible light, as well as a device for visual observation advantageously with an appropriate protective filter, and combined observation and recording devices 2 comprising, for example, a camera, a monitor and a video system. A variable IR filter 24 is advantageously inserted ahead of the latter to perform a corresponding protective function.

In an arrangement of this kind it is possible to use as light sources various lasers connected to the microscope 1 by a compact coupling optic. Both the (pulsed) UV laser 3, which operates for example in the near UV, and the (continuously operating) IR laser 4, which operates for example in the near IR, must be capable of very sharp (diffraction-limited) focusing, that is, have a minimal beam divergence. As long as they satisfy these prerequisites, the lasers can be very diverse in construction; small, compact lasers for laboratory studies or the like are particularly suitable.

For example, a nitrogen laser or a frequency-multiplied IR laser can be used as the UV laser 3, while as the IR laser 4 a diode-pumped Nd:YAG laser or Nd:YLF laser with appropriate performance can be used. Here it should be taken into account that particles movably contained in fluid in the object holder 22, but without intrinsic motility, can be trapped with a low-power laser output, whereas higher power is required to trap particles with their own dynamics or particles in highly viscous solutions. As mentioned previously, for the coupling of two IR laser beams that can be moved independently of One another it is possible to use either two diode-pumped Nd:YAG lasers or one flashlamp-pumped Nd:YAG laser with high output, as indicated schematically in the drawing.

An important aspect of the apparatus in accordance with the invention is that each beam of the lasers 3 and 4 is provided with its own diverging optic 10, 11 or 12, 13 or 14, 15, respectively, each of which can be displaced in three dimensions, in particular three mutually orthogonal directions, as indicated schematically in the drawing. These diverging optics expand the beam passing through them to such an extent that the beam diameter just fills or slightly exceeds the back-facing aperture of the objective 21 of the microscope 1. For example, these diverging optics can comprise two planoconvex lenses or one planoconvex and one planoconcave lens of suitable focal length.

Insofar as coordinate directions are indicated in the drawing for the diverging optics 10, 11 or 12, 13 or 14, 15, these refer to the situation in the object holder 22, such that the x-y plane is perpendicular to the plane of the drawing and the z direction is orthogonal to them and lies within the plane of the drawing.

By displacing one of the diverging optics 12, 13 or 14, 15 in the x-y plane, therefore, the site of fixation of the optical trap in the x-y plane can be altered, whereas a movement in the z direction causes the focus to shift perpendicularly to the x-y plane, so that the particle caught in the optical trap is moved out of the (original) observation plane.

The diverging optic 10, 11 for the UV laser 3 operates correspondingly. Displacement of the diverging optic 10, 11 in the x-y direction changes the site at which particles in the object plane are influenced. A movement in the z direction causes a defocusing in this direction with respect to the observation plane. Hence processing can optionally be carried out either in the focus/object plane or outside this focus/object plane.

In addition or alternatively, it is possible to rotate or tilt the components 8, 9 and 20 in planes transverse to the plane of the drawing, in order to move the associated beams in the x-y plane.

The object holder 22 is displaceable in the directions of the x, y and z axes in a manner known per se, to achieve suitable positioning. The objective 21 in turn is displaceable at least in the z direction.

In the illustrated embodiment the observation and recording devices are arranged so as to operate with transmitted light. The arrangement can of course be such that these observation and recording devices 2 and 23, respectively, are positioned on one side of the microscope 1 and the light source 17 for the observation light is behind the microscope 1, in the direction of the beam, so that it is possible to operate with reflected light.

The previously described apparatus can be used for many applications in which small particles are to be processed and manipulated under simultaneous observation. Fixation of particles at one or more sites is achieved by turning on or off the two IR laser beams from the IR laser 4 or, where appropriate, a larger number of beams produced by analogous extension of the apparatus: for example, by using the beam splitter 16 or the beam splitter 19 to generate additional beams, each of which is coupled to the system by way of its own diverging optic. The system allows the beams in the first wavelength range, i.e. from the IR laser 4, those in the second wavelength range, i.e. from the UV laser 3, and those of the observation light all to be focused in a given object plane at the onset of manipulation and observation, regardless of their wavelengths; that is, they are focused in a particular x-y plane of the object holder. Therefore the individual beams can be influenced independently of one another in order to move particles within the object holder 22 and to process them at a specifically targeted position within their three-dimensional extent, for example by utilizing the UV laser 3 described above.

In this process, one way to produce movements in the x-y plane is to displace the object holder 22 in the x-y direction, in which case all the particles it contains move simultaneously in this plane. Movement in this direction can also be brought about by operating at least, one of the diverging optics 12, 13 or 14, 15 or tilting least one mirror surface of the components 8, 9, 20, so that single particles can be moved independently of one another.

Movements in the z direction can be produced in various ways; one way is to move the object holder 22 in the z direction relative to the objective 21, and another is to move the objective 21 in the z direction relative to the object holder. In both these cases the focusing is preserved for the visible observation light.

Independently of the preceding, at least one of the diverging optics 12, 13 and 14, 15 can be operated in the z direction, so as to enable tilting or rotation of an object in the object holder 22. In this way a three-dimensional object can be observed and processed in various imaginary planes of section through the object.

Because the diverging optic 10, 11 for the UV laser 3 can be moved independently of the preceding optics, the processing can he optionally carried out in the focus/observation plane or outside the focus/observation plane.

The apparatus described in the preceding enables use of the IR laser beams to position an object in a plane other than that of the object holder, with no need for the object to be "clamped" to the object holder, because fixation is brought about merely by the IR laser beams generated by the IR laser 4. It is thus possible simultaneously to observe and process one or more freely movable objects in a simple and reliable manner.

In the embodiment described above an arrangement is employed in which all of the light beams generated by each individual light source are passed, deflected and focused practically within the same plane, from the light-generating devices on. The various beams are sent to the object holder 22 by way of a common deflection mirror 7 and the objective 21. This feature enables an especially compact arrangement, which also guarantees that the apparatus will function reliably.

It is of course also possible to distribute the various components of the optical devices in a three-dimensional arrangement, but then in most cases it becomes necessary to employ spherical or parabolic mirrors, in order to direct each beam onto the object holder 22 in the desired manner. This can be useful or desirable for particular applications, if compact structure is not of primary importance.

I claim:

1. Apparatus for the manipulation, processing and observation of small particles, comprising at least one first laser (4) that generates light beams in a first wavelength range, a first optical device (12, 13, 14, 15, 21) for focusing the beams in said first wavelength range with sufficient convergence to form an optical trap in a predetermined region, an object holder (22) to contain particles, a light source (17) for observation light, and observation and recording devices (1, 2, 23) with which to observe particles in the object holder (22) and to record their behavior, and at least one second laser (3) to generate light beams in a second wavelength range, and a second optical device (10, 11, 21) for focusing the beams in said second wavelength range with sufficient convergence to manipulate particles present in the object holder (22), wherein for each of the light beams from the first laser (4) and the second laser (3) its own diverging optic (12, 13, 14, 15, 10, 11) is provided, which in each case is adjustable in three dimensions, including along three orthogonal coordinates (x, y, z), in such a manner that the optical devices (10, 11, 12 to 15, 21) for the beams in the first wavelength range, for the beams in the second range, and for the beams of the observation light can each be positioned and focused separately and independently of one another; and wherein the beams in the first wavelength range, the beams in the second wavelength range and the beams of the observation light are focused at the beginning of manipulation and observation in the same object plane (x-y plane) of the object holder (22), regardless of their wavelengths, wherein the respective beams can be influenced independently of one another in order to achieve movements of the particles within the object holder (22) and to process them at a specifically targeted position within their three-dimensional extent, and wherein the focusing can be preserved for the visible observation light.

2. Apparatus as claimed in claim 1, wherein each of the first lasers (4) is a laser with wavelength that can be adjusted where appropriate; and wherein each of the second lasers (3) is a UV laser with wavelength that can be adjusted where appropriate.

3. Apparatus as claimed in claim 2, wherein at least one of said first lasers is an IR laser.

4. Apparatus as claimed in claim 2, wherein at least one of said second lasers is a pulsed UV laser.

5. Apparatus as claimed in claim 1, 2, 3, or 4, wherein each of the first lasers (4) is a Nd:YAG laser, a Nd:YLF laser or a titanium-sapphire laser, and wherein each of the second lasers (3) is a nitrogen laser, a frequency-multiplied IR laser or a pumped dye laser.

6. Apparatus as claimed in claim 1, wherein all of the first lasers (4) and the second lasers (3) are arranged in the same tower (5) but can be positioned and adjusted independently of one another.

7. Apparatus as claimed in claim 1, wherein the light beam of the first laser (4) is divided by a beam splinter (16) that produces at least first and second beams in the first wavelength range, which pass separately over at least part of their paths and are then directed onto the object in the Object bolder (22).

8. Apparatus as claimed in claim 7, wherein the beam splitter (16) is a polarizing beam spitter that generates a first beam of s-polarized light and a second beam of p-polarized light and adjusts the phase shift between these two beams, and wherein the percentage relationship between the intensities of the individual beams in the first wavelength range is adjustable.

9. Apparatus as claimed in claim 1, wherein mirrors and beam splitters (8, 9, 20) are provided in the path of the beams from the first laser (4) and the second laser (3) can be rotated or tilted independently of the diverging optics.

10. Apparatus as claimed in claim 1, wherein the beam of the observation light can be focused on the object in the object holder (22) by adjusting the objective (21) and/or the object holder (22) along the optical axis (z direction); and wherein the site of observation for the beam of the observation light in the object plane (x-y plane) can be adjusted by displacing the object holder (22) in an x-y plane within the object plane.

11. Apparatus as claimed in claim 1, wherein in a path of the beam from each of the first lasers (4) and second lasers (3) a beam attenuator (18, 25) is provided, with which the beams in the associated wavelength range can be attenuated, in preset steps or continuously, before they are directed onto the object in the object holder (22).

12. Apparatus as claimed in claim 11, wherein the light beams in the first wavelength range and the light beams in the second wavelength range are directed onto the relevant object in the object holder (22) through a common objective (21) by way of a common mirror (7).

13. Apparatus as claimed in claim 12, wherein the light beams generated by the beam-generating devices and subsequently treated, deflected and focused on the relevant object all lie in substantially the same first plane; and wherein the object holder (22) is positioned in a second plane (x-y plane) perpendicular to the first plane; and wherein the mirrors or beam splitters (7, 8, 9, 19, 20) to deflect the individual light beams are likewise arranged in planes substantially perpendicular to the first plane.

14. A method for the manipulation, processing and observation of small particles, in which the objects in an object holder (22) are fixed in an optical trap by means of at least one first laser (4) that generates light beams in a first wavelength range and the objects are observed and/or their behavior is recorded with observation and recording devices (1, 2, 23), and in which at least one second laser (3) is used, which generates light beams in a second wavelength range that are focused with sufficient convergence to manipulate particles present in the region of the object holder (22), wherein for each of the beams from the first laser (4) and the second laser (3) its own diverging optic (12, 14, 14, 15, 10, 11) is used, which in each case is adjustable in three dimensions, including along three orthogonal coordinates (x, y, z), in such a manner that the light beams in the first wavelength range and the beams of the observation light can each be adjusted in the object plane (x-y plane) and focused in the axial direction (z direction) with separate optical devices, independently of one another; and wherein the beams in the first wavelength range, the beams in the second wavelength range and the beams of the observation light are focused at the beginning of manipulation and observation in the same object plane (x-y plane) of the object holder (22), regardless of their wavelengths, wherein the respective beams can be influenced independently of one another in order to achieve movements of the particles within the object holder (22) and to process them at a specifically targeted position within their three-dimensioned extent, wherein the focusing can be preserved for the visible observation light.

15. Method as claimed in claim 14 wherein a particle captured in the optical trap of each of the first lasers (4) can be shifted within the object plane;

(a) by displacing at least one light beam in the first wavelength range in the x-y direction and/or, (b) by displacing the object holder (22) in the x-y direction in the object plane, whereby in case (a) only the captured particle is moved and in case (b) all particles except for the captured particle are moved.

16. Method as claimed in claim 14 or 15, wherein a particle captured in the optical trap of each of the first lasers (4) can be shifted within the object plane;

(a) by displacing the focus position of at least one light beam in the first wavelength range in the z direction and/or (b) by displacing the objecting (21) and/or the object holder (22) in the z direction, whereby in case (a) the captured particle is moved out of the chosen observation plane and in case (b) the captured particle remains in the chosen observation plane.

17. Method as claimed in claim 14, wherein when at least two separate light beams in the first wavelength range are used, rotation of a particle in the optical trap is brought about (a) by leaving one beam in its starting position and moving the other beams in the x-y direction, or (b) by leaving one beam in its starting position and moving the other beam in the z direction, or (c) by moving at least two light beams in opposite directions or over different distances along the z axis, or (d) by combinations of the movements according to (a), (b) and (c).

18. Method as claimed in claim 14, wherein the manipulation of the particles with the light beams in the second wavelength range is carried out in an arbitrarily selectable x-y plane of the object bolder (22), and the observation plane can be situated in the same plane or another plane parallel to it.

19. Method as claimed in claim 14, wherein to fix the particles in the optical trap visible or IR laser beams are used and for manipulation of the particles UV laser beams are used.

20. Method as claimed in claim 14, wherein the UV laser beams comprise pulsed UV laser beams.

21. Method as claimed in claim 14, wherein all the light beams can be directed simultaneously onto the relevant object in the object holder (22) through the same objective (21).

22. Method as claimed in claim 14, wherein all the light beams for controlling the manipulation and/or observation can be adjusted in their intensity and/or be turned on and off independently of one another.

23. Apparatus as claimed in claim 1, wherein the small particles comprise biological particles.

24. Method as claimed in claim 14, wherein the small particles comprise biological particles.

* * * * *